(12) United States Patent
Farkas

(10) Patent No.: US 7,052,683 B2
(45) Date of Patent: May 30, 2006

(54) COMPOSITION TO DETOXIFY FORMALDEHYDE IN GASEOUS STATE, IN AQUEOUS SOLUTIONS, AND TO PROTECT HUMAN CELL LINES AGAINST FORMALDEHYDE

(76) Inventor: Gabriel J. Farkas, 9843 Forbes Ave., Northridge, CA (US) 91343-1700

( * ) Notice: Subject to any disclaimer, the term of this patent is extended or adjusted under 35 U.S.C. 154(b) by 214 days.

(21) Appl. No.: 10/719,841

(22) Filed: Nov. 24, 2003

(65) Prior Publication Data
US 2005/0113627 A1  May 26, 2005

(51) Int. Cl.
| | |
|---|---|
| *A61L 9/01* | (2006.01) |
| *A61L 9/00* | (2006.01) |
| *A61L 11/00* | (2006.01) |
| *C09K 3/00* | (2006.01) |
| *A61K 31/17* | (2006.01) |
| *A61K 31/715* | (2006.01) |
| *A61K 31/131* | (2006.01) |
| *A01N 1/00* | (2006.01) |
| *A01N 47/28* | (2006.01) |

(52) U.S. Cl. .................. 424/76.1; 252/188.2; 252/193; 422/1; 422/4; 422/5; 424/75; 424/76.5; 424/76.8; 514/2; 514/58; 514/554; 514/556; 514/562; 514/574; 514/588; 514/669

(58) Field of Classification Search .................. 424/75, 424/76.1, 76.5, 76.8; 252/188.1, 188.2, 193; 514/588, 574, 669, 58, 2, 554, 556, 974; 422/1, 4, 5; 588/318
See application file for complete search history.

(56) References Cited

U.S. PATENT DOCUMENTS

| | | | | |
|---|---|---|---|---|
| 4,929,700 | A | * 5/1990 | Halenbeck et al. | .......... 530/351 |
| 5,837,159 | A | * 11/1998 | Farkas et al. | ............... 252/193 |
| 6,001,274 | A | * 12/1999 | Farkas et al. | ............... 252/184 |

OTHER PUBLICATIONS

Derwent abstract acc-No. 1982-97101E.*
The Merck Index Twelfth Edition 1996, pp. 458, 761 and 762.*

* cited by examiner

Primary Examiner—John Pak
Assistant Examiner—Ernst Arnold

(57) ABSTRACT

A chemical compound is disclosed herein for performing a complex enzymatic neutralization and fixation of formaldehyde, providing a method for instantaneous neutralization of formaldehyde vapors and offering a complete and rapid control of incidental releases, and a complete protection of workers against airborne formaldehyde during the course of their work. The compound includes alkanolamine, for instantaneous reaction with formaldehyde, and for absorbing hydrogen sulfide and carbon dioxide from the air, and a human protein, which reacts with airborne formaldehyde and forms the major enzyme involved in formaldehyde oxidation in oral mucosa. The compound also contains cyclodextrins for inclusion complexation of all the components of spent and/or unused aqueous formaldehyde solutions.

1 Claim, No Drawings

COMPOSITION TO DETOXIFY FORMALDEHYDE IN GASEOUS STATE, IN AQUEOUS SOLUTIONS, AND TO PROTECT HUMAN CELL LINES AGAINST FORMALDEHYDE

BACKGROUND OF THE INVENTION

1. Field of the Invention

The present invention relates to the field of detoxification and neutralization of hazardous substances, and more particularly to a novel chemical compound incorporating a detoxifying combination of substances that are rapidly neutralizing and fixating toxic formaldehyde vapors, forming an adduct with formaldehyde, an enzyme, which plays a vital role in the defense against formaldehyde in oral buccal tissue and oral epithelial cell lines. The compound also absorbs hydrogen sulfide and carbon dioxide from the ambient air.

2. Brief Description of the Prior Art

Concentrated formaldehyde solutions before being diluted to preparation solutions contain up to 37% formaldehyde w/v. Currently available neutralizing products are intended for use with 10% formalin solutions (3.7% formaldehyde only, the neutralization/application time is being over 20 minutes. Products for instant detoxification of formaldehyde vapors, and especially products offering a potential, enzymatic defense against formaldehyde are not available.

During the course of their work workers (such as embalmers) are exposed to the extremely toxic formaldehyde vapors. Personal exposures to formaldehyde in mortuaries have been documented as 0.5 to 8.72 parts formaldehyde per million parts of air (ppm).

The permissible exposure limits for formaldehyde in the workplace covered by OSHA standards are 0.75 ppm measured as an 8-hour time-weighted average.

Therefore, a long-standing need exists to provide an unique detoxifier which not only neutralizes airborne formaldehyde at various concentrations, but serves as the prime guardian against formaldehyde in human oral tissue.

SUMMARY OF THE INVENTION

Accordingly, the above problems and difficulties are obviated by the present invention, which provides a novel composition that detoxifies formaldehyde vapors, it offers an enzymatic defense against formaldehyde in human tissues and human epithelial cell lines. The compound also modifies the chemical activity of other hazardous constituents by molecular encapsulation, complexation, and stabilization.

Therefore, it is among the primary objects of the present invention to provide a novel, fast-reacting neutralizer of the toxic formaldehyde vapors. Another object of the present invention is to provide a natural detoxifier of the inhaled and/or ingested formaldehyde vapors.

Yet another object of the present invention is to provide a fast reacting neutralizer of aqueous formaldehyde solutions of various concentrations.

Yet another object of the present invention is to provide a fast reacting neutralizer for incidental releases of formaldehyde solutions.

Yet another object of the present invention is to provide a cleaner, healthier and safer work environment.

DESCRIPTION OF THE PREFERRED COMPOSITION

The composition/formulation of the present invention which is believed to be novel is set forth with particularity in the appended claims. The present invention, both as to its organization and manner of operation, together with further objects and advantages thereof, may best be understood with reference to the following description.

One alkanolamine, the Tris(hydroxymethyl) aminomethane (Tris Amino), in aqueous solution, is employed for rapid neutralization of formaldehyde vapors, and their aqueous solutions various concentrations. This substance is well suited for the proposed application because the TRIS molecule reacts with two molecules of formaldehyde.

Glutathione (g-glutamylcysteineglycine, GSH), an antioxidant and enzyme cofactor is used for detoxifying the airborne and/or inhaled and ingested formaldehyde vapors. The "reduced glutathione" is a tripeptide, consisiting of three aminoacids-glutaric acid, cysteine and glycine. Enzyme systems synthesize it, utilize it, and regenerate it as per the gamma-glutamyl cycle. An adduct forms spontaneously between formaldehyde and GSH in aqueous solutions. This enzyme is the glutathione-dependent formaldehyde dehydrogenase, which offers a potential enzymatic defense against formaldehyde (formaldehyde detoxification) in oral buccal tissue specimens, and oral epithelial cell lines. GSH is used by the liver to detoxify formaldehyde and plays a key role in Phase I and Phase II detoxification reactions.

Urea is used as another formaldehyde neutralizer, the urea lattice is a strong host for formaldehyde.

Cyclodextrins are used for inclusion complexation for all components of formaldehyde solutions (including buffering agents). These are a group of cavity-containing cyclic compounds, provide a method of molecularly encapsulate, and thereby modify the apparent physical and chemical properties of the guest molecules, giving rise to beneficial modifications of guest molecules not otherwise achievable (e.g. solubility enhancement and psyhical insulation of incompatible substances. Their potential guest lists for molecular inclusion include alcohols, aldehydes, gases, fatty acids, etc.

What is claimed is:

1. A chemical composition for use in rapid detoxification of toxic formaldehyde vapors from incidental releases of unused or spent formaldehyde solutions of various concentrations or absorption of hydrogen sulfide from ambient air, comprising tris(hydroxymethyl)aminomethane, urea, beta-cyclodextrin and reduced glutathione.

* * * * *